United States Patent [19]
Yokota

[11] Patent Number: 5,973,737
[45] Date of Patent: Oct. 26, 1999

[54] APPARATUS HAVING AN EYE CONTROL UNIT

[75] Inventor: Hideo Yokota, Yokohama, Japan

[73] Assignee: Canon Kabushiki Kaisha, Tokyo, Japan

[21] Appl. No.: 08/744,429

[22] Filed: Nov. 7, 1996

Related U.S. Application Data

[63] Continuation of application No. 08/281,664, Jul. 28, 1994, abandoned.

[30] Foreign Application Priority Data

Jul. 30, 1993 [JP] Japan ..................................... 5-190106

[51] Int. Cl.⁶ .................................................. H04N 5/225
[52] U.S. Cl. ........................................... 348/341; 333/762
[58] Field of Search ............................ 348/31, 169, 341, 348/762, 766, 767, 333; 396/51; 250/222.1; 359/487, 489; 362/228; H04N 5/232

[56] References Cited

U.S. PATENT DOCUMENTS

| | | | |
|---|---|---|---|
| 4,695,163 | 9/1987 | Schachar | 356/369 |
| 5,036,347 | 7/1991 | Tsunekawa et al. | 354/400 |
| 5,084,807 | 1/1992 | McKechnie | 362/228 |
| 5,182,443 | 1/1993 | Suda et al. | 250/201.2 |
| 5,214,466 | 5/1993 | Nagano et al. | 354/402 |
| 5,225,862 | 7/1993 | Nagano et al. | 354/62 |
| 5,245,371 | 9/1993 | Nagano et al. | 354/62 |
| 5,253,008 | 10/1993 | Konishi et al. | 354/402 |
| 5,280,312 | 1/1994 | Yamada et al. | 351/211 |
| 5,296,888 | 3/1994 | Yamada | 354/402 |
| 5,298,927 | 3/1994 | Konishi et al. | 351/211 |
| 5,302,819 | 4/1994 | Kassies | 250/222.1 |
| 5,579,079 | 11/1996 | Yamada et al. | 396/51 |

FOREIGN PATENT DOCUMENTS 4323974  11/1992  Japan ............................. H04N 5/225

OTHER PUBLICATIONS

Wolff et al.—Liquid Crystal Polarization Camera—Proc. IEEE Workshop on App. of Computer Vision—Dec. 1992—pp. 120–127.

*Primary Examiner*—Wendy Garber
*Assistant Examiner*—Aung S. Moe
*Attorney, Agent, or Firm*—Fi8tzpatrick, Cella, Harper & Scinto

[57] ABSTRACT

An apparatus is provided with an illuminating light source for illuminating a user's eye and an optical system for causing, Purkinje image and an anterior eye part image created by the illumination to be formed on a solid state image pickup element, and is designed such that the influence of extraneous light is mitigated in the output signal of the solid state image pickup element by the use of a polarizing element for selecting the polarization characteristic of the image light received by the solid state image pickup element.

27 Claims, 9 Drawing Sheets

ON

OFF

APPARATUS HAVING AN EYE CONTROL UNIT

This application is a continuation of application Ser. No. 08/281,664 filed Jul. 28, 1994, now abandoned.

BACKGROUND OF THE INVENTION

1. Field of the Invention

This invention relates to the optical system of an information input unit usable in the finder of an ordinary still camera, a video camera or an optical instrument for viewing, a computer, a machine tool, a patient's will displaying apparatus or the like to detect a utilizer's visual axis and control the instrument.

2. Related Background Art

There have heretofore been proposed various visual axis detecting apparatuses for detecting what position on an observation surface an observer (utilizer) is observing.

For example, a Japanese patent publication describes a system in which a beam of light from a light source is projected onto the anterior eye part of an examinee and the visual axis of the examinee is found by the utilization of a corneal reflection image based on the reflected light from the examinee's cornea and the imaged position of the examinee's pupil. FIG. 14 of the accompanying drawings illustrates a visual axis detecting method.

In FIG. 14, the reference numeral 1004 designates a light source such as a light-emitting diode emitting infrared light to which the examinee is insensible. The light source 1004 is disposed in the focal plane of a light projecting lens 1006.

The infrared light emitted from this light source 1004 is made into parallel light by the light projecting lens 1006, is reflected by a half mirror 1005 and illuminates the cornea 1001 of an eyeball 1000. At this time, corneal reflection image (Purkinje first image) d based on part of the infrared light reflected by the surface of the cornea 1001 passes through the half mirror 1005, is condensed by a light receiving lens 1007 and re-forms the corneal reflection image d at a position d' on an image sensor 1009. Also, beams of light from the end portions a and b of an iris 1003 are directed onto the image sensor 1009 through the half mirror 1005 and the light receiving lens 1007, and forms the images of the end portions a and b at positions a' and b' on the image sensor.

When the angle of rotation $\theta$ of the optical axis t of the eyeball relative to the optical axis S of the light receiving lens 1007 is small, if the Z coordinates of the end portions a and b of the iris 1003 are defined as Za, Zb, the coordinates Zc of the center position c of the iris 1003 is expressed as $$Zc \cong (Za+Zb)/2.$$

Also, if the Z coordinates of the created position d of the corneal reflection image are Zd and the distance between the center of curvature 0 of the cornea 1001 and the center c of the iris 1003 is Loc, the angle of rotation $\theta$ of the optical axis t of the eyeball substantially satisfies the relational expression that $$Loc \cdot \sin \theta \cong Zc - Zd.$$

Therefore, by detecting the positions of the corneal reflection image d projected onto the image sensor 1009 and the end portions a and b of the iris 1003, the angle of rotation $\theta$ of the optical axis t of the eyeball can be found.

In the above-described example of the prior art, the illuminating light is parallel light, but alternatively, divergent light may be used.

FIG. 15 of the accompanying drawings illustrates the principle of an eye axis detecting method when divergent light is used as the illuminating light.

Infrared lights emitted from light sources 1004a and 1004b are transmitted through light projecting lenses 1006a and 1006b, whereafter they widely illuminate the cornea 1001 of the eyeball 1000 while diverging. At this time, corneal reflection images e and f based on beams of light of the infrared lights illuminating the eyeball 1000 which are reflected by the surface of the cornea 1001 are re-formed at positions e' and f' on the image sensor 1009 through the light receiving lens 1007. These images e' and f' are the projected images of the corneal reflection images e and f created by a set of light sources 1004a and 1004b. The midpoint of the projected images e' and f' is substantially coincident with the projected position, onto the image sensor 1009, of the cornea image created when illuminating means is disposed on the optical axis t. Also, the infrared light diffused and reflected by the surface of the iris 1003 is directed onto the image sensor 1009 through the light projecting lens 1007 to form an iris image. The light projecting lens may be omitted.

In a calculating device 1010, from the coordinates Za' and Zb' of the end portions a and b of the iris 1003 of the eyeball 1000 and the coordinates Ze' and Zf' of the corneal reflection images on the image sensor 1009, the angle of rotation $\theta$ of the eyeball 1000 can be found in accordance with the relatival expression that $$\beta \cdot Loc \cdot \sin \theta \cong (Za'+Zb')/2 - (Ze'+Zf')/2,$$

where $\beta$ is the magnification of the light receiving optical system. In order to correct the calculated angle of rotation of the optical axis into the angle of rotation of the visual axis, some correction is effected, but this is well known and therefore need not be described.

By thus detecting the direction of the visual axis of the observer's eye to be examined, for example, in a video camera, what position on the finder thereof the observer is observing can be known, and for example, on the basis of that information, the focus of the photo-taking lens of the video camera can also be adjusted to an object corresponding to that position.

Now, assuming that sunlight or intense illuminating light enters the eyeball from between a visual axis detecting apparatus and the face and illuminates, for example, half of the eyeball, a luminance signal indicative of the right side of the iris may become greater in intensity than the left side as shown in FIG. 13 of the accompanying drawings to thereby hide the signal f" of the Purkinje image f and make the accurate detection of the visual axis difficult.

As a method for compensating for this, it would occur to mind to make the intensity of the light illuminating the eyeball high, but this could not always be said to be a good method in as much as there will newly arise a problem that Purkinje image obtained by applying intense light to the eyeball will become large and hide the information of the edge of the pupil.

SUMMARY OF THE INVENTION

One aspect of the application is to ensure corrent detection to be effected even in a state in which undesired ambient light which is a hindrance to detection is present.

Another aspect of the application is to prevent, in an apparatus for detecting the direction of the visual axis (gaze point) by the use of the image of the anterior eye part and a reflected light source image by the cornea, undesired light from irradiating the face to thereby make the detection difficult or reduce the accuracy of the detection.

Still another aspect of the application is to provide illuminating means for illuminating an operator's eye, image detecting means for detecting reflected image light obtained by said illuminating means, optical means for directing the reflected image light to said image detecting means, and polarization control means for selectively controlling the polarization characteristic of said reflected image light to said image detecting means, thereby detecting the direction of the visual axis well.

It is desirable that said polarization control means be disposed in an optical path leading from said operator's eye to said image detecting means or the optical path leading from said illuminating means to said operator's eye.

Also, it is desirable that said polarization control means be comprised of a polarizing filter for selectively transmitting polarized light therethrough, or a liquid crystal panel, or a combination of them.

On the other hand, it is desirable that said liquid crystal panel be driven time-serially or areally, and in that case, the direction of the visual axis can be detected more highly accurately in such a manner that in association with the driving of the liquid crystal panel, a desired image is detected by the image detecting means.

BRIEF DESCRIPTION OF THE PREFERRED EMBODIMENTS

Figure 1A:
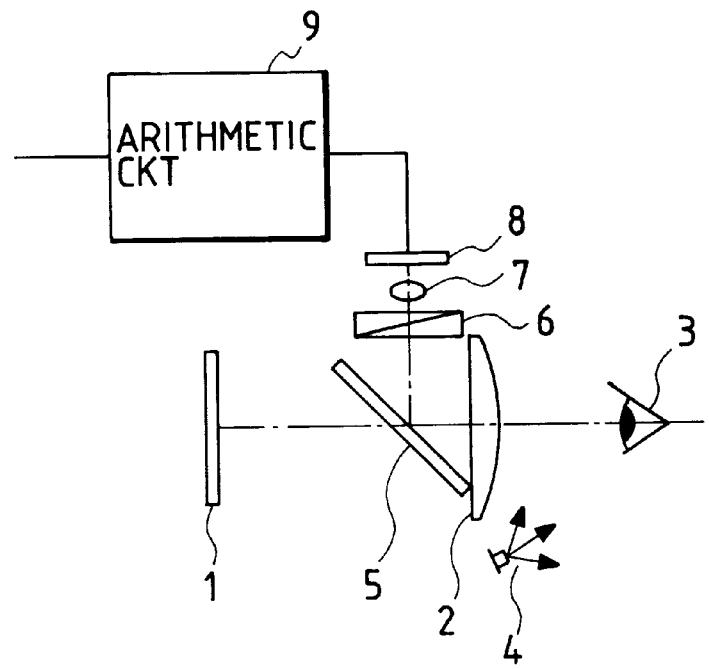
FIG. 1A shows a first embodiment of the present invention.

Referring to FIG. 1A which shows a first embodiment of the present invention, the reference numeral 1 designates an image display such as a liquid crystal panel on which an image being observed is displayed or formed, the display plate of a CRT or the focusing screen of a camera. The object field photographed by an objective lens, not shown, or a character, a symbol and a picture made by a signal generator appear on the image display 1. The reference numeral 2 denotes an eyepiece for enlargedly observing the image of the image display 1 therethrough, and the reference numeral 3 designates a utilizer's eyeball.

The reference numeral 4 denotes an illuminating light source such as an infrared light emitting diode for illuminating the eyeball 3. It is to be understood that two such light sources are disposed toward the eyeball in a direction perpendicular to the plane of the drawing sheet of FIG. 1A. The reference numeral 5 designates an optical path separating element such as an edge filter, a half mirror or a dichroic mirror for separating an observation system and a visual axis detection system. The reference numeral 6 denotes a polarizing element such as a polarizing filter for passing only light in a particular direction of polarization therethrough. The polarizing element 6 is disposed in the reflection side optical path by the optical path separating element 5, and in the present embodiment, it is disposed forwardly of an imaging lens 7, but alternatively, it may be disposed rearwardly of the imaging lens 7. The reference numeral 8 designates a solid state image pickup element of the area type such as a CCD. The imaging lens 7 and the eyepiece 2 form the two Purkinje images of the anterior eye part of the eyeball 3 as viewed from the front thereof and the light source 4 on the solid state image pickup element 8. The reference numeral 9 denotes an arithmetic (calculating) circuit for the visual axis direction. The arithmetic circuit 9 can process the Purkinje images converted into electrical signals and the information of the iris in accordance with the above-described method, can output a signal regarding the visual axis direction or a character or a symbol being gazed at, and can make a body instrument, not shown, execute a predetermined function.

The method of determining the visual axis direction is not limited what has been described above, but may be another method. Also, a microcomputer on the body instrument side may be diverted as the arithmetic circuit.

Figure 1B:
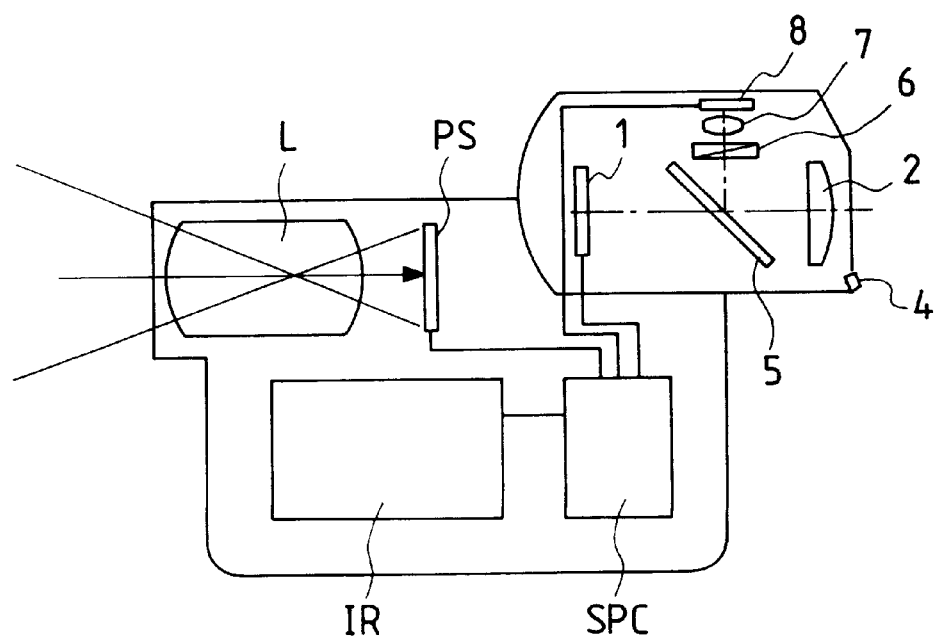
FIG. 1B shows the first embodiment as it is incorporated into a video camera.

FIG. 1B depicts a case where the present embodiment is a video camera. In FIG. 1B, the letter L designates a photo-taking zoom lens, and PS denotes a photosensor for receiving an image formed by the zoom lens. SPC designates a signal processing circuit for processing the output signal of the photosensor PS and recording it on an information recording medium. The output of the photosensor PS is displayed as an image on the image display 1. On the other hand, the output from the image pickup element 8 is converted into gaze point information by the signal processing circuit SPC, and the gaze point is superposed on the image on the image display 1 and is displayed as a spot. Further, the information of the gaze point is used to designate a gaze point corresponding position on the photosensor PS, and conventional signal processing for TV-AF is done with regard to this position. The focus adjustment of the zoom lens L is effected by the use of a signal regarding the thus obtained focus state.

Figure 2:
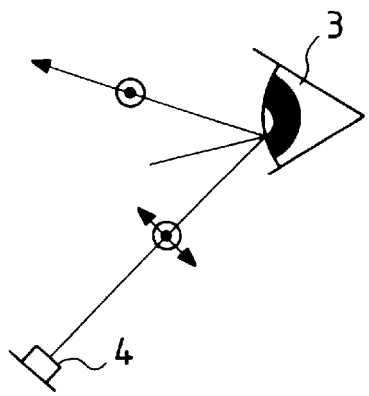
FIG. 2 illustrates the reflection of light by a cornea.

The optical action of the apparatus of FIG. 1A will now be described. First, as shown in FIG. 2, the Purkinje image is formed by the light emitted from the illuminating light source 4 being reflected by the surface of the cornea of the eyeball 3, and by selecting the angle of incidence of the light onto the surface of cornea to an angle greater than 0°, the rate of the polarized component of the light forming the Purkinje image can be varied. As the angle of incidence is made greater and approximate to the so-called Brewster angle, the reflected light becomes light including much of an S-polarized component (in FIG. 2, a direction perpendicular to the plane of the drawing sheet). On the other hand, the light reflected by the iris is light scattered on the surface of the iris and therefore, light including all polarized components is reflected.

Figure 3:
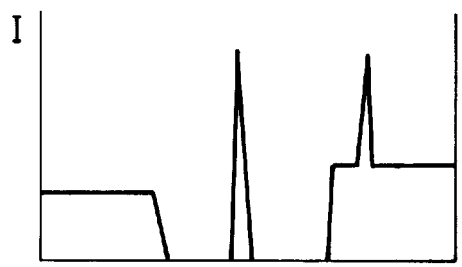
FIG. 3 shows the output by the first embodiment.

Accordingly, if the direction of the polarization axis of the polarizing element 6 is preset so as to pass the S-polarized component therethrough, the light from the Purkinje image will intactly pass through the polarizing element 6 and enter the solid state image pickup element 8, whereas the light from the iris and others will be intercepted by the polarizing element 6 except for the S-polarized component and therefore, the iris portion will likewise be decreased even if the sunlight enters the eye, and the Purkinje image will become discernible even if the Purkinje image and the iris overlap each other as indicated by a one-line output signal in FIG. 3.

Figure 4:
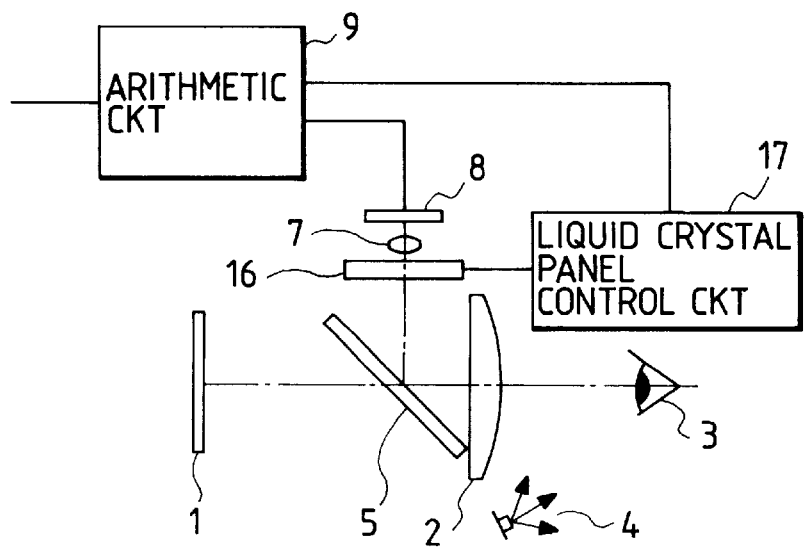
FIG. 4 shows a second embodiment of the present invention.
Figure 5A:
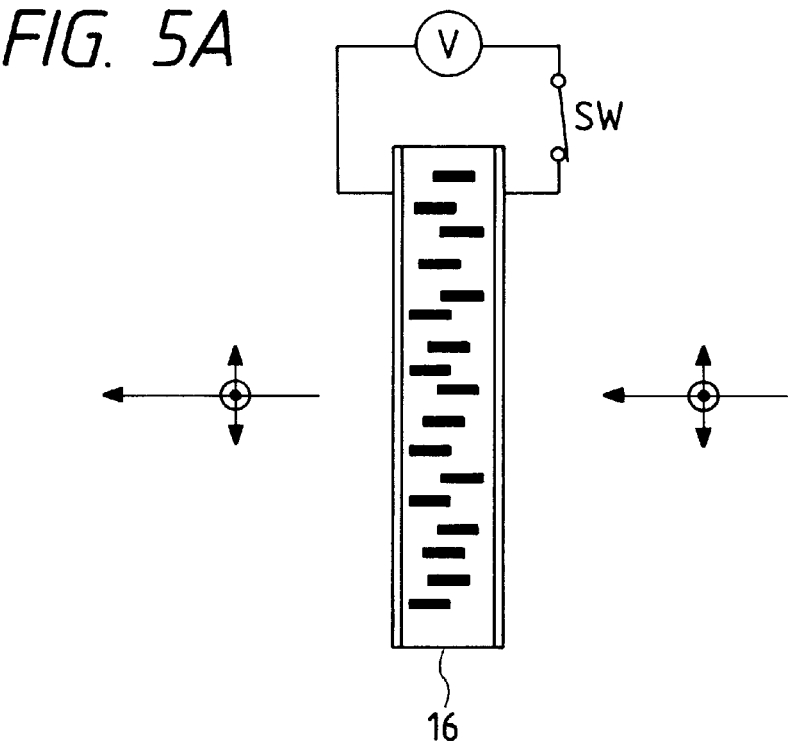
FIGS. 5A and 5B illustrate the driving of EC liquid crystal in the second embodiment.
Figure 5B:
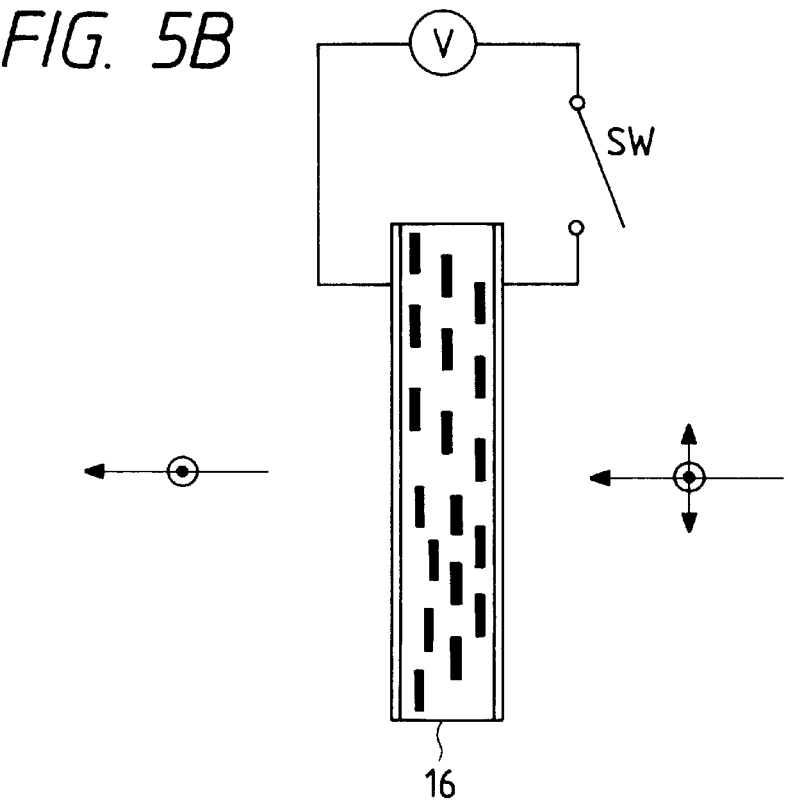

FIGS. 4, 5A and 5B are for illustrating a second embodiment of the present invention which uses a liquid crystal panel of the guest-host type as a polarizing element.

The reference numeral 1 designates an image display, the reference numeral 2 denotes an eyepiece, the reference numeral 4 designates an illuminating light source, the reference numeral 5 denotes an optical path separating element for separating an observation system and a visual axis detection system, the reference numeral 16 designates a polarizing element such as a liquid crystal panel of the guest-host type, and the reference numeral 7 denotes an imaging lens cooperating with the eyepiece 2 to form the image of the eyeball. The reference numeral 8 designates an image pickup element for converting the information of the image of the eyeball into an electrical signal, and the reference numeral 9 denotes a visual axis arithmetic circuit for calculating the direction of the visual axis on the basis of the eyeball image information from the image pickup element 8. The reference numeral 17 designates a liquid crystal panel control circuit for controlling the liquid crystal panel. The liquid crystal panel control circuit 17 is designed to be controlled by the visual axis arithmetic circuit.

As the guest-host liquid crystal, use is made of a dichroic dye such as azo dye dissolved in nematic liquid crystal molecules, whereby light is transmitted without being absorbed by the dye in a state in which a voltage is applied to the liquid crystal panel 17 (FIG. 5A), and light in a particular direction of polarization is absorbed by the dye in a state in which a voltage is not applied to the liquid crystal panel 17 (FIG. 5B). An active polarizing filter can be constituted thereby, and the direction of polarization of Purkinje image and the direction of polarization in the absorbing state of the liquid crystal panel are disposed so as to be orthogonal to each other, and the liquid crystal panel control circuit varies the absorbing state of the liquid crystal panel in conformity with the image pickup state of the eyeball image, whereby the brightness of the iris can be adjusted without affecting the Purkinje image.

Figure 6:
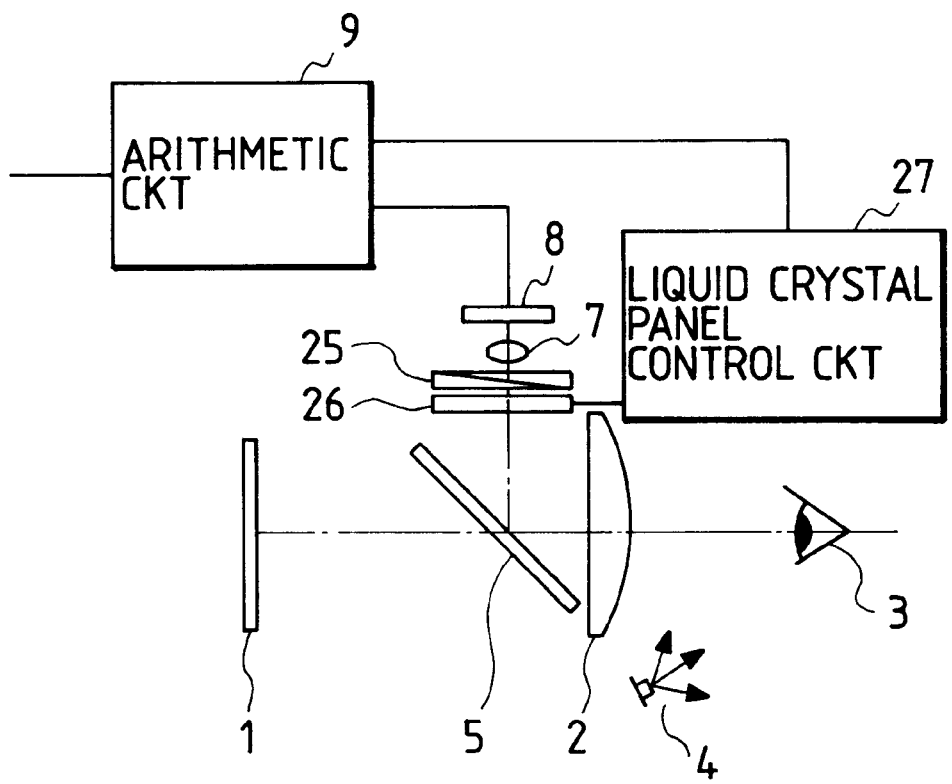
FIG. 6 shows a third embodiment of the present invention.

FIG. 6 shows a third embodiment of the present invention in which a polarizing element and a liquid crystal panel of the twist nematic type are combined together so that the detection of Purkinje image and the detection of edge of the iris may be separately effected. The reference numeral 1 designates an image display, the reference numeral 2 denotes an eyepiece, the reference numeral 4 designates an illuminating light source, the reference numeral 5 denotes an optical path separating element for separating an observation system and a visual axis detection system, the reference numeral 25 designates a polarizing element such as a polarizing filter, and the reference numeral 26 denotes a liquid crystal panel of the twist nematic type. The reference numeral 7 designates an imaging lens cooperating with the eyepiece 2 to form the image of the eyeball, the reference numeral 8 denotes an image pickup element for converting the information of the image of the eyeball into an electrical signal, and the reference numeral 9 designates a visual axis arithmetic circuit for calculating the direction of the visual axis on the basis of the eyeball image information from the image pickup element 8. The reference numeral 27 denotes a liquid crystal panel control circuit for controlling the liquid crystal panel. The liquid crystal panel control circuit 27 is controlled by the arithmetic circuit in accordance with a predetermined time chart.

The polarizing element 25 and the liquid crystal panel 26 are disposed on the optical path of the visual axis detection system so that the polarizing element direction of orientation is such that the direction of polarization of Purkinje image turns by 90°, and the polarizing element is designed to be parallel or perpendicular to the direction of polarization of the Purkinje image.

Figure 8A:
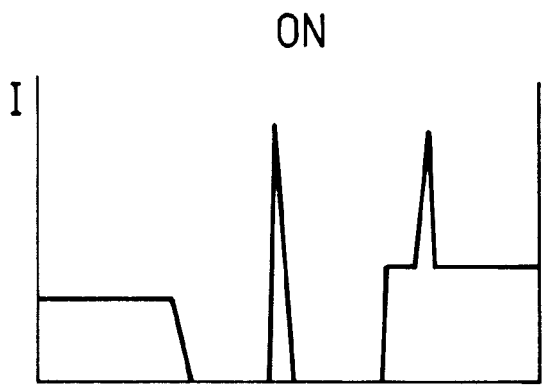
FIGS. 8A and 8B show the output by the third embodiment.
Figure 8B:
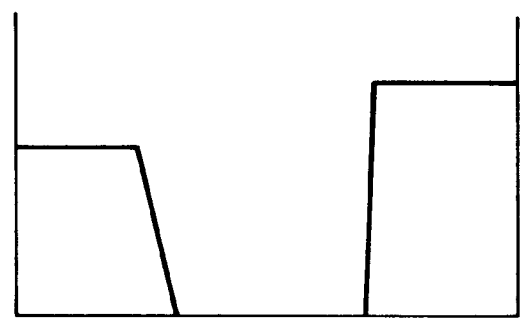
Figure 7A:
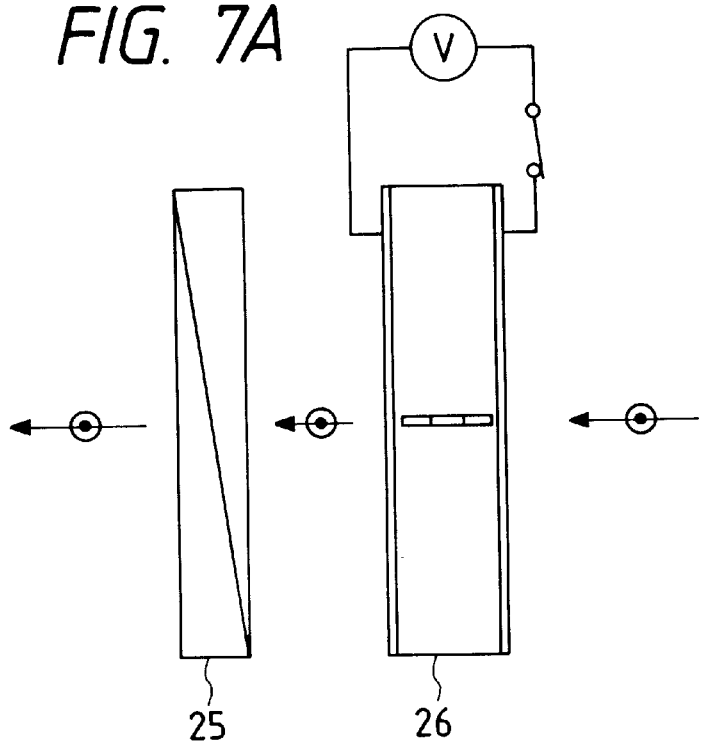
FIGS. 7A and 7B illustrate the driving of TN liquid crystal in the third embodiment.
Figure 7B:
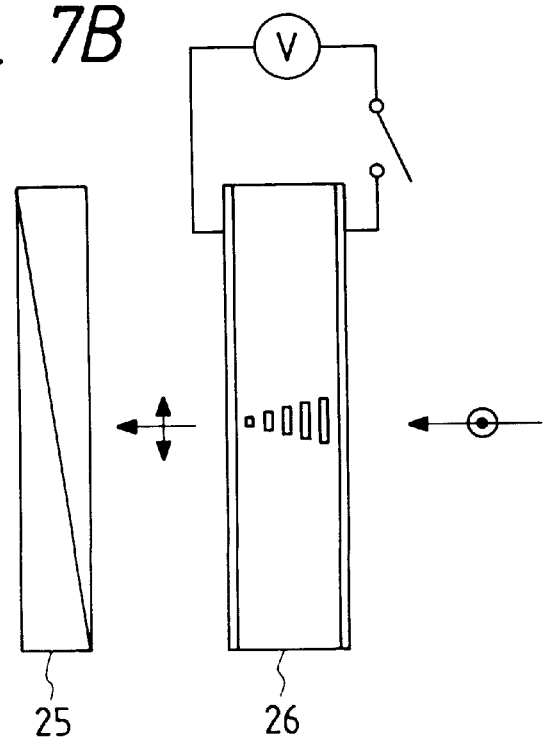

In a state in which a voltage is applied to the liquid crystal panel shown in FIG. 7A (ON), the direction of polarization of the incident Purkinje image turns by 90° in the liquid crystal panel and the Purkinje image emerges therefrom, and is transmitted through the polarizing element and is picked up; in a state in which a voltage is not applied to the liquid crystal panel of FIG. 7B (OFF), the incident Purkinje image emerges without its direction of polarization being changed, and is intercepted by the polarizing element. Thereby, in the state in which the liquid crystal panel is ON, the Purkinje image and the pupil image (iris) are picked up (FIG. 8A), and in the state in which the liquid crystal panel is OFF, the Purkinje image is cut and only the pupil image (iris) is picked up (FIG. 8B). If the direction of polarization in which the polarizing element transmits the Purkinje image therethrough is turned by 90°, the image pickup states during the ON and OFF of the liquid crystal panel will become reverse.

Figure 9A:
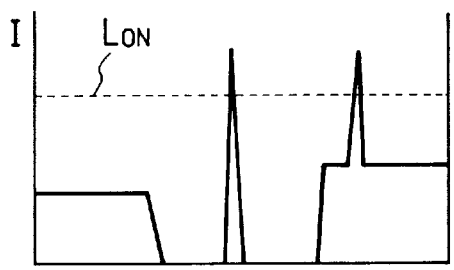
FIGS. 9A and 9B show the output by the third embodiment.
Figure 9B:
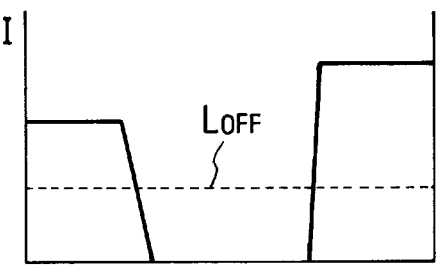
Figure 10A:
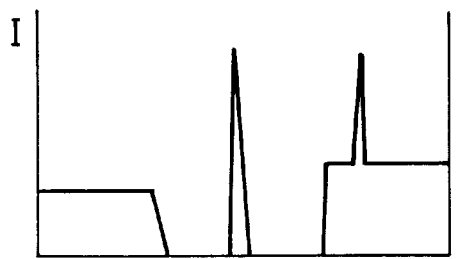
FIGS. 10A and 10B show the output by the third embodiment.
Figure 10B:
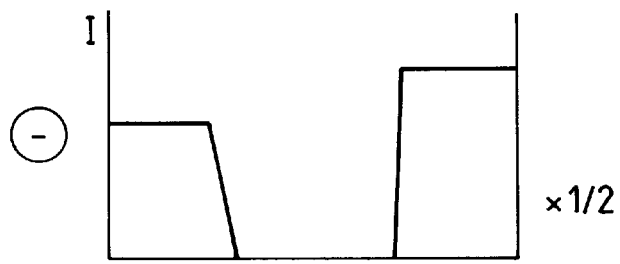
Figure 10C:
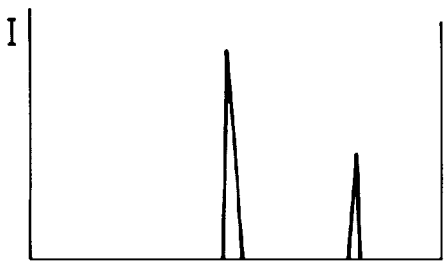
FIG. 10C is a combined output graph.

FIGS. 9A and 9B show the images picked up in the ON state and OFF state of the liquid crystal panel and a one-line output signal. The edge of the pupil is detected from an image in which only the pupil has been picked up, and the Purkinje image is detected from an image in which the pupil has also been picked up. When detecting the Purkinje image, a particular threshold value (LOFF) may be determined from the image of the pupil alone in the signal processing circuit, and the Purkinje image may be taken out in such a manner that it is binarized by a threshold value (LON) determined by the comparison with the threshold value LOFF. Also, as shown in FIGS. 10A, 10B and 10C, the image of the pupil alone from the Purkinje image may be subtraction-processed in the signal processing circuit.

Figure 11:
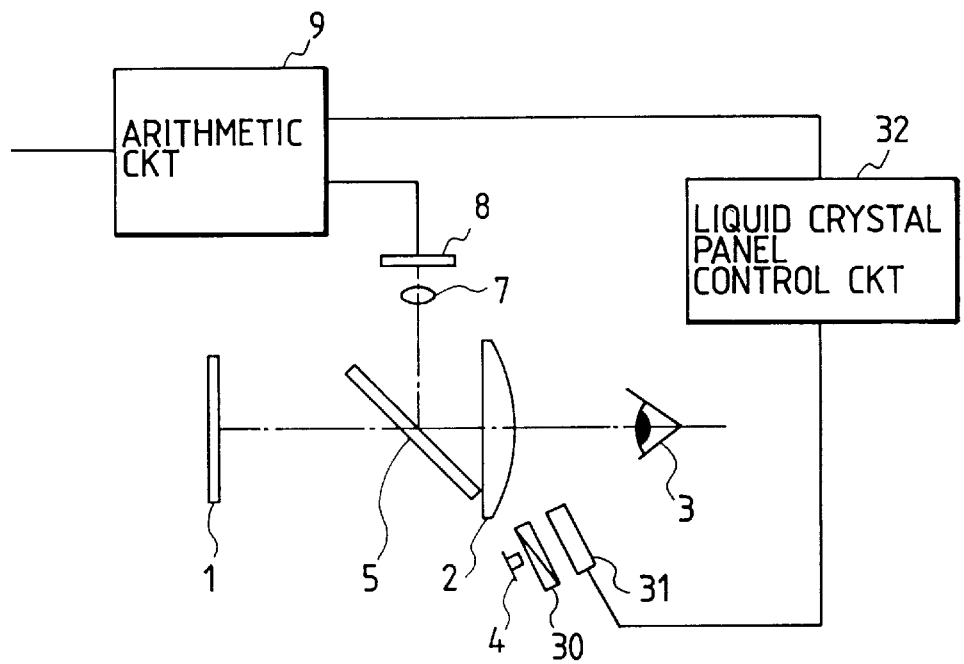
FIG. 11 shows a fourth embodiment of the present invention.
Figure 13:
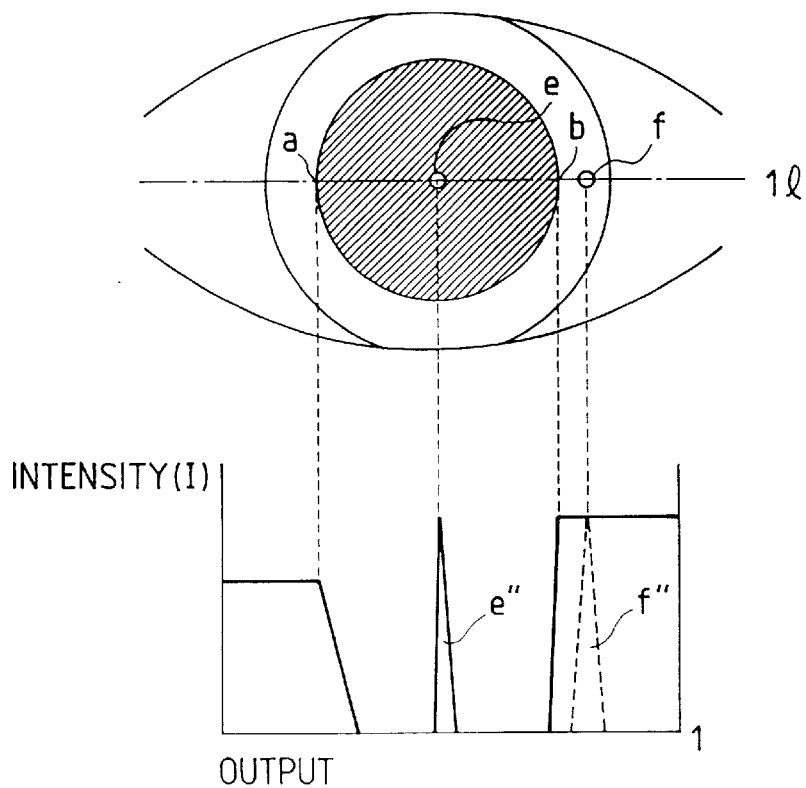
FIG. 13 shows a problem peculiar to visual axis detection.

FIG. 11 shows a fourth embodiment of the present invention in which a liquid crystal panel of the twist nematic type is provided on the emergence side of a light source so as to sequentially change over the direction of polarization of illuminating light so that the detection of the pupil edge and the detection of the Purkinje image may be separately effected.

The reference numeral 1 designates an image display, the reference numeral 2 denotes an eyepiece, the reference numeral 4 designates an illuminating light source, the reference numeral 30 denotes a first polarizing element such as a polarizing filter, and the reference numeral 31 designates a liquid crystal panel of the twist nematic type. The reference numeral 5 denotes an optical path separating element for separating an observation system and a visual axis detection system, the reference numeral 7 designates an imaging lens cooperating with the eyepiece 2 to form the image of the eyeball, the reference numeral 8 denotes an image pickup element for converting the information of the image of the eyeball into an electrical signal, the reference numeral 9 designates a visual axis arithmetic circuit for calculating the direction of the visual axis on the basis of the eyeball image information from the image pickup element 8, and the reference numeral 32 denotes a liquid crystal panel control circuit for controlling the liquid crystal panel 31.

Figure 12A:
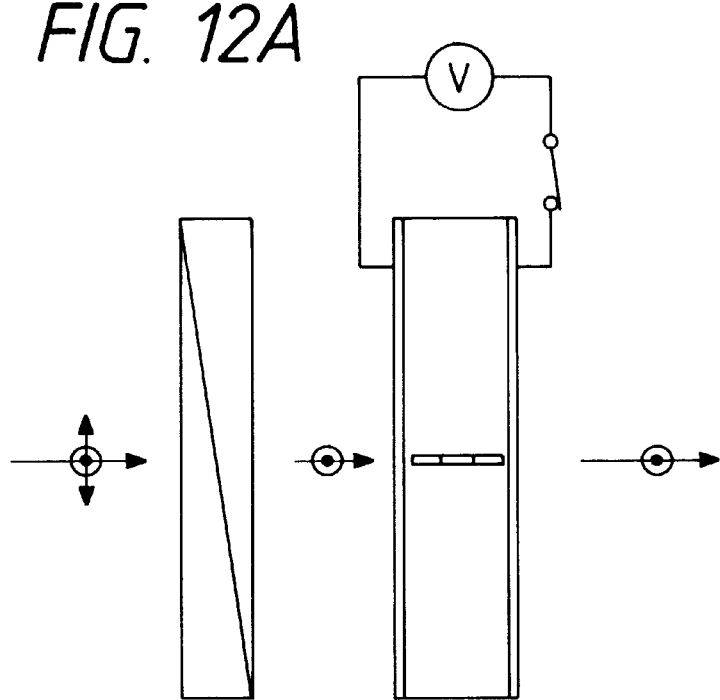
FIGS. 12A and 12B illustrate the driving of TN liquid crystal in the fourth embodiment.
Figure 12B:
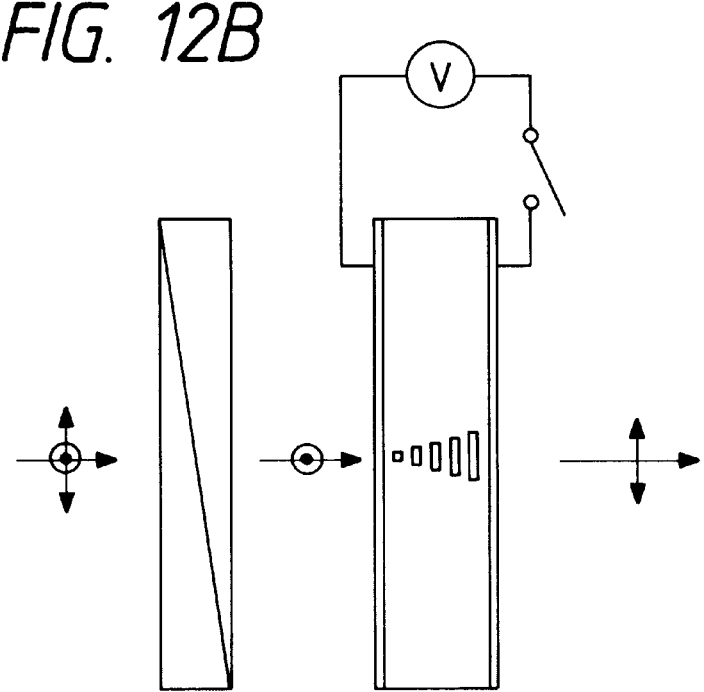
Figure 14:
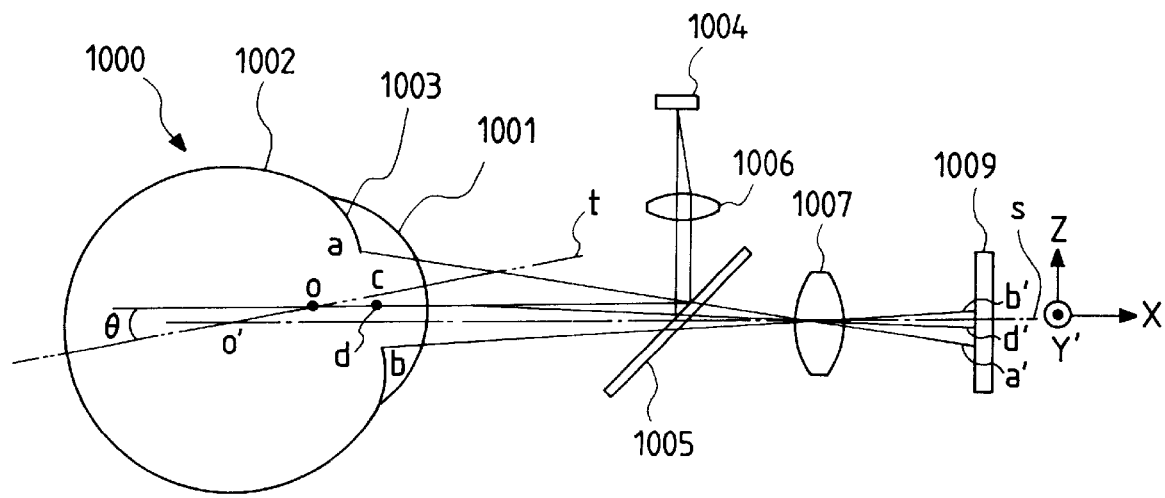
FIG. 14 is a side view showing an example of the prior art.
Figure 15:
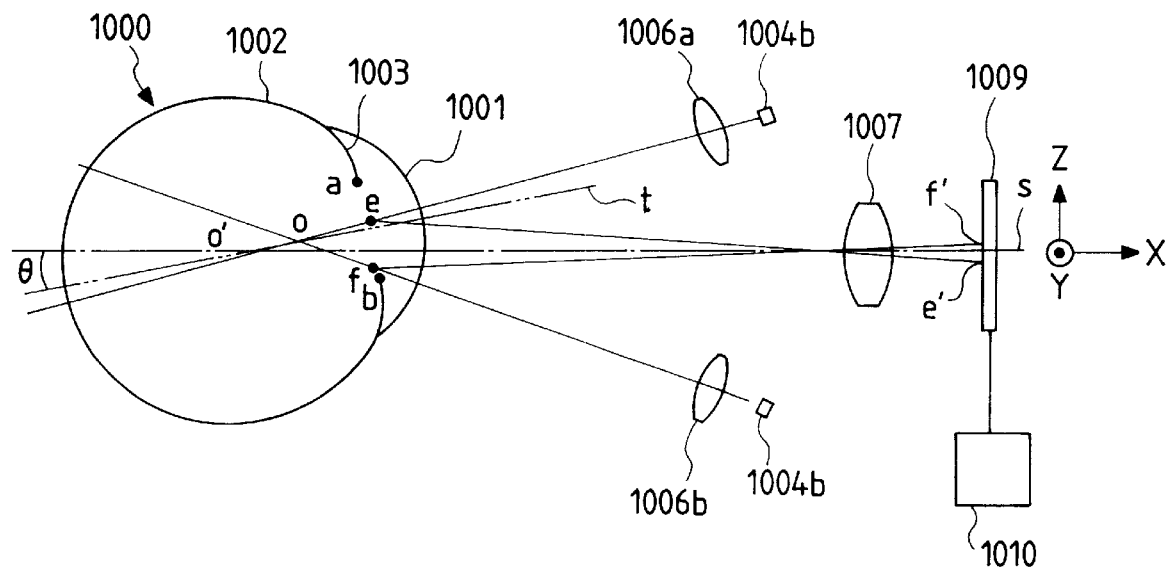
FIG. 15 is a front view showing another example of the prior art.

The polarizing element 30 and the liquid crystal panel 31 are disposed between the illuminating light source 4 and the eyeball 3 so that the polarizing element 30 may be on the illuminating light source side of the liquid crystal panel 31. As shown in FIGS. 12A and 12B, it becomes possible to change over the direction of polarization of the illuminating light to the direction of P-polarization and the direction of S-polarization with respect to the reflecting surface of the cornea by ON and OFF of the liquid crystal panel. The eyeball is first illuminated by an S-polarized component to obtain a Purkinje image and a pupil image, and then the S-polarized component is changed over to a P-polarized component. When the eyeball is illuminated by the P-polarized component, the reflection by the cornea does not occur and therefore, it becomes possible to pick up the pupil image alone, and processing similar to that in the third embodiment becomes possible.

In the above-described embodiment, the liquid crystal panel, etc., as polarization control means, are disposed in the optical path on the illumination side or the light reception side, but alternatively, polarization control means may be provided on both of the illumination side and the light reception side and the two may be appropriately synchronized with each other to thereby obtain a similar effect.

According to the present invention as described above, even when undesired light impinges on the utilizer's eye, the detection of information necessary for the detection of the visual axis is possible and correct detection can be realized.

Particularly, by controlling the intensity of the Purkinje image and the intensity of the pupil edge image independently of each other, the lack of the image information by extraneous light and the lack of the image information by the mutual interference between the Purkinje image and the pupil edge image can be prevented and more highly accurate detection of the visual axis is made possible.

What is claimed is:

1. A view finder comprising:
   means for forming an image to be viewed;
   a light source for illuminating an eye from an oblique direction, said light source being disposed under an eyepiece of said view finder;
   a sensor for receiving a reflection light from the eye to change the reflection light into a signal in accordance with an intensity distribution of the reflection light; and
   an analyzer for extracting an S-polarized component from the reflection light to make the S-polarized component be directed to said sensors,
   wherein said analyzer is configured to make the S-polarized component be directed to said sensor so as to pass a Purkinje image to said sensor while decreasing an amount of reflection light from an iris of the eye that passes to said sensor.

2. The finder according to claim 1, further comprising a lens for converging the reflection light onto said sensor.

3. The finder according to claim 1, further comprising a dichroic mirror disposed obliquely in front of said means for forming an image to reflect the reflection light toward a side of said sensor.

4. The finder according to claim 1, wherein said light source comprises means for supplying a polarized light beam and means for rotating a polarization direction of the polarized light beam.

5. The finder according to claim 1, wherein said light source comprises a polarizing plate for forming a polarized light beam and a twisted nematic type liquid crystal device for rotating a polarization direction of the polarized light beam.

6. The finder according to claim 5, wherein said light source illuminates the eye so that an angle of illumination becomes a Brewster angle.

7. A view finder according to claim 1, wherein said light source illuminates the eye so that an angle of illumination becomes a Brewster angle.

8. A view finder according to claim 1, wherein said sensor is disposed above the eyepiece of said view finder.

9. A view finder according to claim 8, wherein said light source is fixedly disposed under the eyepiece of said view finder.

10. A view finder comprising:
    means for forming an image to be viewed;
    a light source for illuminating an eye alternatively with a P-polarized light beam and an S-polarized light beam from an oblique direction, said light source being disposed under an eyepiece of said view finder; and
    a sensor for receiving a reflection light from the eye to change the reflection light into a signal in accordance with an intensity distribution of the reflection light,
    wherein a Purkinje image is detected in accordance with a difference between an output of said sensor when the eye is illuminated with the P-polarized light beam and an output of said sensor when the eye is illuminated with the S-polarized light beam, and
    wherein when the eye is illuminated with the P-polarized light beam, the reflection light forms an image of a pupil without forming the Purkinje image on said sensor, and when the eye is illuminated with the S-polarized light beam, the reflection light forms an image of the pupil and the Purkinje image on said sensor.

11. The finder according to claim 10, further comprising a lens for converging the reflection light onto said sensor.

12. The finder according to claim 10, further comprising a dichroic mirror disposed obliquely in front of said means for forming an image for reflecting the reflection light toward a side of said sensor.

13. The finder according to claim 10, wherein said analyzer comprises a liquid crystal device for changing over between (a) a first condition wherein only the S-polarized component is transmitted therethrough and (b) a second condition wherein a P-polarized component and the S-polarized component of the reflection light are transmitted therethrough.

14. The finder according to claim 10, wherein said analyzer comprises a set of a liquid crystal device and a polarizing plate for changing over between (a) a first condition for extracting the S-polarized component and (b) a second condition for extracting a P-polarized component of the reflection light.

15. The finder according to claim 14, wherein the Purkinje image is detected in accordance with a first signal obtained through said sensor in the first condition and a pupil of the eye is detected in accordance with a second signal obtained through said sensor in the second condition.

16. The finder according to claim 14, wherein the Purkinje image is detected in accordance with a first signal obtained through said sensor in the first condition and a second signal obtained through said sensor in the second condition.

17. The finder according to any of claims 10 through 12, 13 through 16, 1 through 3, or 4 through 6, wherein the finder is disposed in an image taking apparatus.

18. A view finder according to claim 10, wherein said light source illuminates the eye so that an angle of illumination becomes a Brewster angle.

19. An optical apparatus comprising:
   a light source for illuminating an eye, said light source being disposed under an eyepiece of a view finder of said optical apparatus;
   a sensor for receiving a reflection light from the eye to change the reflection light into a signal in accordance with an intensity distribution of the reflection light; and
   an analyzer for extracting an S-polarized component from the reflection light to make the S-polarized component be directed to said sensor;
   wherein said analyzer is configured to make the S-polarized component be directed to said sensor so as to pass a Purkinje image to said sensor while decreasing an amount of reflection light from an iris of the eye that passes to said sensor.

20. An optical apparatus according to claim 19, wherein said light source illuminates the eye so that an angle of illumination becomes a Brewster angle.

21. The apparatus according to claim 19, further comprising a lens for converging the reflection light onto said sensor.

22. The apparatus according to claim 19, wherein the Purkinje image is detected in accordance with an output of said sensor.

23. An optical apparatus comprising:
   a light source for illuminating an eye alternatively with a P-polarized light and an S-polarized light, so that an angle of illumination becomes a Brewster angle; and
   a sensor for receiving a reflection light from the eye to change the reflection light into a signal in accordance with an intensity distribution of the reflection light,
   wherein a Purkinje image is detected in accordance with a difference between a first output of said sensor when the eye is illuminated with the P-polarized light beam and a second output of said sensor when the eye is illuminated with the S-polarized light beam, and
   wherein an image of a pupil is detected by using one of the first and second outputs, and
   wherein when the eye is illuminated with the P-polarized light beam, the reflection light forms an image of the pupil without forming the Purkinje image on said sensor, and when the eye is illuminated with the S-polarized light beam, the reflection light forms an image of the pupil and the Purkinje image on said sensor.

24. The apparatus according to claim 23, further comprising a lens for converging the reflection light onto said sensor.

25. An optical apparatus comprising:
   a light source for illuminating an eye from an oblique direction with a first polarized light and a second polarized light being mutually different, wherein the first polarized light and the second polarized light are a P-polarized light and an S-polarized light, said light source comprising means for supplying the first polarized light and means for changing the first polarized light into the second polarized light by rotating a polarization direction of the first polarized light, said light source being disposed under an eyepiece of a view finder of said optical apparatus; and
   a sensor for receiving a reflection light from the eye to change the reflection light into a signal in accordance with an intensity distribution of the reflection light,
   wherein a Purkinje image is detected in accordance with a difference between a first output of said sensor when the eye is illuminated with the P-polarized light beam and a second output of said sensor when the eye is illuminated with the S-polarized light beam, and an image of a pupil is detected by using one of the first and second outputs, and
   wherein when the eye is illuminated with the P-polarized light beam, the reflection light forms an image of the pupil without forming the Purkinje image on said sensor, and when the eye is illuminated with the S-polarized light beam, the reflection light forms an image of the pupil and the Purkinje image on said sensor.

26. The apparatus according to claim 25, further comprising a lens for converging the reflection light onto said sensor.

27. An optical apparatus according to claim 25, wherein said light source illuminates the eye so that an angle of illumination becomes a Brewster angle.

* * * * *